United States Patent
Baratz et al.

(10) Patent No.: US 7,152,471 B2
(45) Date of Patent: Dec. 26, 2006

(54) METHOD AND APPARATUS FOR ASSESSING HAND STRENGTH

(75) Inventors: Mark E. Baratz, Pittsburgh, PA (US); Mark Carl Miller, Oakmont, PA (US); Patrick D. Devanny, Colorado Springs, CO (US); Jufang He, Macdonald, PA (US)

(73) Assignee: Allegheny-Singer Research Institute, Pittsburgh, PA (US)

( * ) Notice: Subject to any disclaimer, the term of this patent is extended or adjusted under 35 U.S.C. 154(b) by 0 days.

(21) Appl. No.: 10/698,781

(22) Filed: Oct. 31, 2003

(65) Prior Publication Data

US 2005/0092083 A1    May 5, 2005

(51) Int. Cl.
*A61B 1/24* (2006.01)

(52) U.S. Cl. .................................................. 73/379.02

(58) Field of Classification Search ............. 73/379.01, 73/379.02, 379.03; 128/782; 482/46, 49, 482/50, 112

See application file for complete search history.

(56) References Cited

U.S. PATENT DOCUMENTS

| | | | | |
|---|---|---|---|---|
| 4,726,248 A | * | 2/1988 | Kawai et al. | 74/471 XY |
| 5,163,443 A | * | 11/1992 | Fry-Welch et al. | 600/595 |
| 5,170,663 A | * | 12/1992 | Kovacevic | 73/379.02 |
| RE35,598 E | * | 9/1997 | Sadoff et al. | 73/379.01 |

* cited by examiner

*Primary Examiner*—Jewel Thompson
(74) *Attorney, Agent, or Firm*—Ansel M. Schwartz

(57) ABSTRACT

An apparatus for assessing a person's hand strength including means for engaging the hand. The apparatus including means for determining the strength of the hand based on a twisting action with the hand of the engaging means relative to the determining means. The engaging means is connected to the determining means. A method for assessing a person's hand strength including the steps of gripping a first object having a first diameter with the hand by the person. There is the step of twisting the first object with the hand. There is the step of measuring torque with a torque sensor, connected to the first object, of the object as it is being twisted by the hand.

9 Claims, 2 Drawing Sheets

METHOD AND APPARATUS FOR ASSESSING HAND STRENGTH

FIELD OF THE INVENTION

The present invention is related to assessing hand strength. More specifically, the present invention is related to assessing hand strength with the use of a torque sensor.

BACKGROUND OF THE INVENTION

Traditionally, the Jamar® dynamometer is used to assess grip strength in the clinical setting as well as in experimental investigation. The dynamometer is limited, however, in that it does not correlate well with activities of daily living. For example, many patients complain of difficulties opening jars, opening doors, and turning keys. These activities require both grip strength while torque is applied. This device is a pistol-shaped apparatus that a patient squeezes. A numerical result can be read from a scale on the side of the device. The present invention is completely different in shape and means of assessment. The present invention is more meaningful to activities of daily living and uses different sizes so that it has distinct advantages to the pistol.

The present invention is a technique to quantify the ability to apply torque with varying moments.

SUMMARY OF THE INVENTION

The present invention pertains to an apparatus for assessing a person's hand strength. The apparatus comprises means for engaging the hand. The apparatus comprises means for determining the strength of the hand based on a twisting action with the hand of the engaging means relative to the determining means. The engaging means is connected to the determining means.

The present invention pertains to a method for assessing a person's hand strength comprising the steps of gripping a first object having a first diameter with the hand by the person. There is the step of twisting the first object with the hand. There is the step of measuring torque with a torque sensor, connected to the first object, of the object as it is being twisted by the hand.

BRIEF DESCRIPTION OF THE DRAWINGS

In the accompanying drawings, the preferred embodiment of the invention and preferred methods of practicing the invention are illustrated in which.

DETAILED DESCRIPTION

Figure 1:
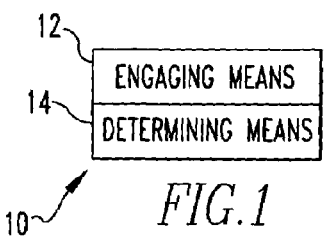
FIG. 1 is a block diagram of the apparatus of the present invention.
Figure 2:
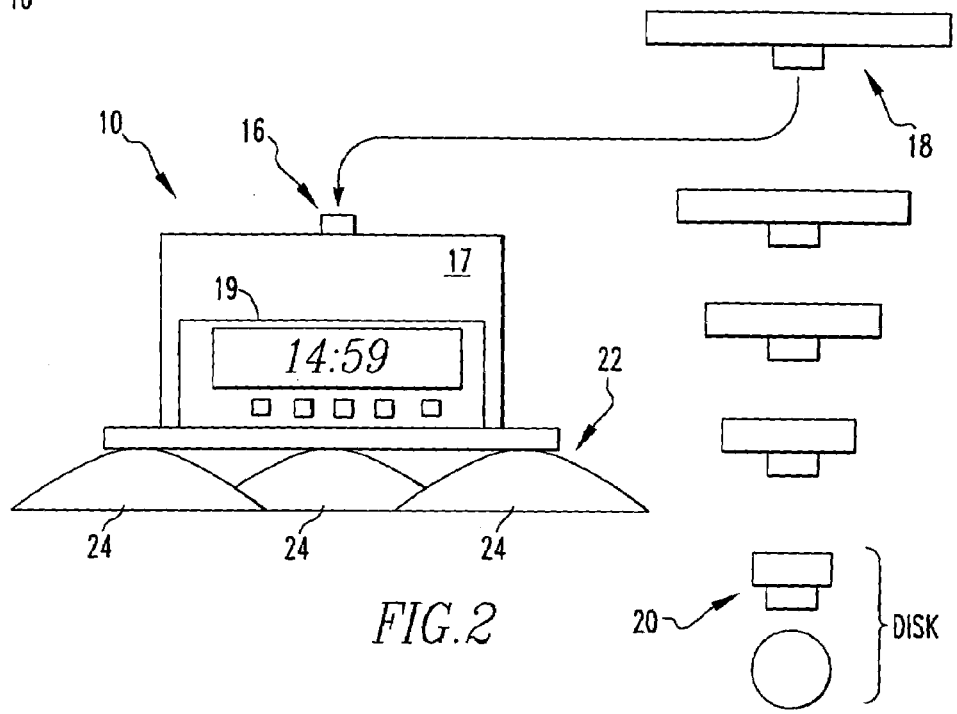
FIG. 2 is a schematic representation of the apparatus.
Figure 3:
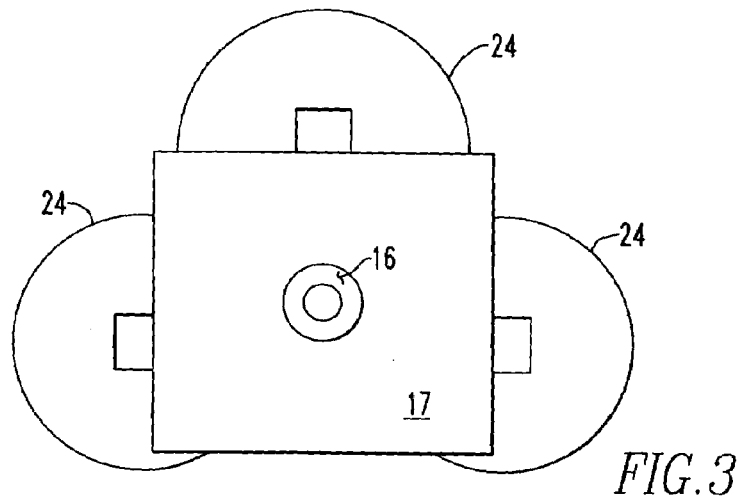
FIG. 3 is an overhead view of the apparatus.
Figure 4:
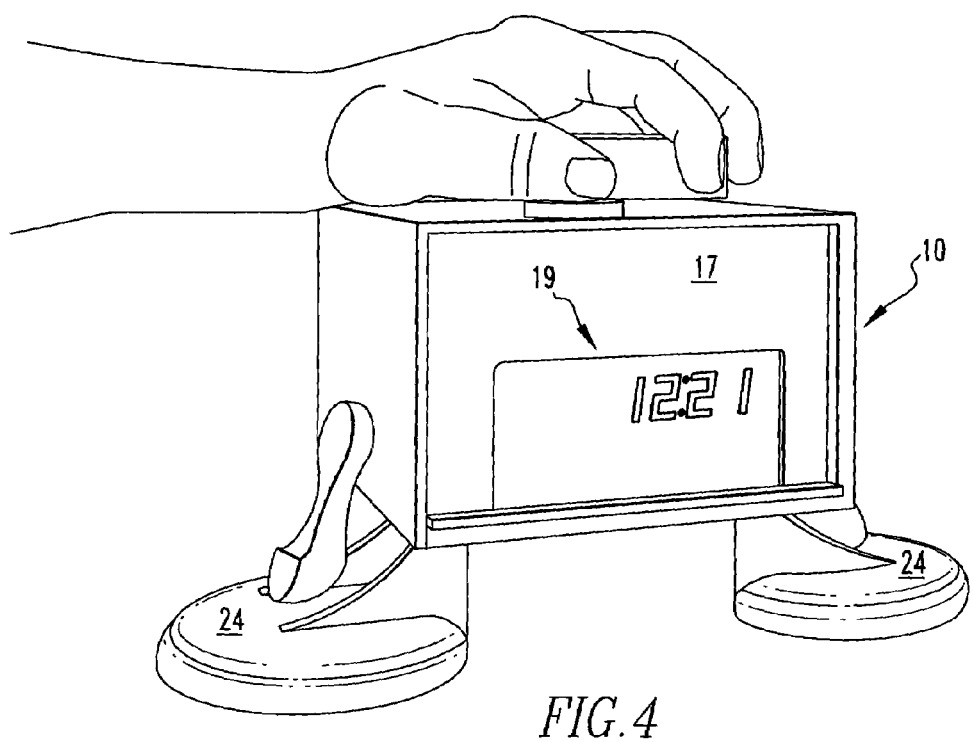
FIG. 4 is a side view of the apparatus.

Referring now to the drawings wherein like reference numerals refer to similar or identical parts throughout the several views, and more specifically to FIGS. 1–4 thereof, there is shown an apparatus 10 for assessing a person's hand strength. The apparatus 10 comprises means for engaging the hand. The apparatus 10 comprises means for determining the strength of the hand based on a twisting action with the hand of the engaging means 12 relative to the determining means 14. The engaging means 12 is connected to the determining means 14.

Preferably, the determining means 14 includes a torque sensor 16. The determining means 14 preferably includes a housing 17 in which the torque sensor 16 is disposed. Preferably, the engaging means 12 includes a first object 18 connected to the torque sensor 16 and extending from the housing 17 having a first diameter which simulates opening a jar with the hand by the person when the person turns the first object 18.

The engaging means 12 preferably includes a second object 20 connected to the torque sensor 16 and extending from the housing 17 having a second diameter less than the first diameter that can replace the first object 18 which simulates turning a key with the hand by the person when the person turns the second object 20. Preferably, the determining means 14 has a display 19 which displays torque sensed by the torque sensor 16. The determining means 14 preferably includes securing means 22 attached to the housing 17 that holds the housing 17 in place. Preferably, the securing means 22 includes suction cups 24. The first object 18 is preferably a first disk and the second object 20 is a second disk.

The present invention pertains to a method for assessing a person's hand strength comprising the steps of gripping a first object 18 having a first diameter with the hand by the person. There is the step of twisting the first object 18 with the hand. There is the step of measuring torque with a torque sensor 16, connected to the first object 18, of the object as it is being twisted by the hand.

Preferably, there is the step of replacing the first object 18 with a second object 20 having a second diameter less than the first diameter, and repeating the gripping, twisting and measuring steps with the second object 20. There is preferably the step of securing a housing 17, from which the first object 18 extends and in which the torque sensor 16 is disposed, in place on to a structure. Preferably, there is the step of displaying the torque measured by the torque sensor 16.

In the operation of the invention, the apparatus 10 is used to conveniently and accurately access hand function. Common activities of daily living can be seriously hampered by thumb injury so that common twisting activities such as turning a key or opening a candy jar can become impossible. In order to quantify thumb injury, the efficacy of surgical procedures and the benefits of rehabilitation, a general-purpose torsional measurement apparatus 10 has been developed.

To perform a test, a subject grips a disk attached to the top of the instrument box and twists. The strength of the twist, the torque, is measured and displayed on the front of the housing 17. The instrument housing 17 is supported by suction cups 24 through a metal frame. The suction cups 24 are used to fix the entire apparatus 10 to a smooth surface and include release levers (levers, not shown). Several sizes of disk are supplied to test different sizes of hand and different tasks, because tasks such as opening jars and turning keys require different grips.

A flanged aluminum shaft of 1.5 cm diameter was bolted to a torque sensing load cell (maximum torque: 5.5 N-m, Model TRT50, Transducer Techniques, Inc.). The load cell was rigidly fixed to a portable platform that could be mounted to a table. Disks of diameters of 1:, 2", 3", 4", and 5" were then bolted to the shaft.

Twenty-seven subjects between the ages of 39 and 59 (ave. 49.1) with no existing upper extremity disorder were tested. Each subject underwent the same testing protocol on two separate occasions. After obtaining history and hand dominance, the subjects were instructed to maximally turn each disk as though they were opening or closing a jar. Maximum value for each disk was recorded.

For the first trial, the average torque (N-m) for disks 1–5, respectively, was 4.2 (1.1–6.6), 11.6 (1.5–22.1), 18.3 (9.5–37.2), 24.7 (12.8–43), 27.8 (14.3–46). For the second trial, the average torque was, respectively, 3.4 (1.3–6.7), 10.4 (5.5–18.6), 16.3 (8.3–31.2), 21.6 (12.3–40.9), 25.8 (13.3–45). Despite the large range which reflects the different strengths of varying subjects, there was a linear trend with increasing disk size and torque.

An analysis of variance using repeated measures showed disk size to be statistically significant ($p<0.001$). Similarly, no statistical significant effect due to test-retest arose ($p=0.532$). A linear regression to determine the effect of disk size showed increasing torque with increasing disk size ($p<0.001$, $R=0.621$).

Many activities of daily living require that an individual twist an object. The apparatus will directly quantify the ability of the user to apply a twisting force, or torque, to objects of different sizes. If a person cannot apply a torque, he/she suffers from at least one of many pathologies that limit this ability. The level of disability can be directly quantified with the device by comparison to normative data.

This new technique of measuring applied torque by varying disk size is reproducible and reliable.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. An apparatus for assessing a person's hand strength comprising:
   means for engaging the hand;
   means for determining the strength of the hand based on a twisting action with the hand of the engaging means relative to the determining means, the engaging means connected to the determining means, the determining means includes a torciue sensor and a housing in which the torque sensor is disposed, the engaging means includes a first object connected to the torque sensor and extending from the housing having a first diameter which simulates opening a jar with the hand by the person when the person turns the first object; and
   an indicator that shows the strength of the hand.

2. An apparatus as described in claim 1 wherein the engaging means includes a second object connected to the torque sensor and extending from the housing having a second diameter less than the first diameter that can replace the first object which simulates turning a key with the hand by the person when the person turns the second object.

3. An apparatus as described in claim 2 wherein the determining means has a display which displays torque sensed by the torque sensor.

4. An apparatus as described in claim 3 wherein the determining means includes securing means attached to the housing that holds the housing in place.

5. An apparatus as described in claim 4 wherein the securing means includes suction cups.

6. An apparatus as described in claim 5 wherein the first object is a first disk and the second object is a second disk.

7. A method for assessing a person's hand strength comprising the steps of:
   gripping a first object having a first diameter with the hand by the person;
   twisting the first object with the hand;
   measuring torque with a torque sensor, connected to the first object, of the object as it is being twisted by the hand; and
   replacing the first object with a second object having a second diameter less than the first diameter, and repeating the gripping, twisting and measuring steps with the second object.

8. A method as described in claim 7 including the step of securing a housing, from which the first object extends and in which the torque sensor is disposed, in place on to a structure.

9. A method as described in claim 8 including the step of displaying the torque measured by the torque sensor.

* * * * *